United States Patent
Cottrell et al.

(10) Patent No.: US 6,889,632 B2
(45) Date of Patent: May 10, 2005

(54) HIGH CONCENTRATION DINOTEFURAN FORMULATIONS CONTAINING METHOPRENE

(75) Inventors: Ian William Cottrell, Basking Ridge, NJ (US); Michael William Lytwyn, East Hanover, NJ (US); Albert Ahn, Short Hills, NJ (US)

(73) Assignee: The Hartz Mountain Corporation, Secaucus, NJ (US)

( * ) Notice: Subject to any disclaimer, the term of this patent is extended or adjusted under 35 U.S.C. 154(b) by 0 days.

(21) Appl. No.: 10/411,720

(22) Filed: Apr. 11, 2003

(65) Prior Publication Data

US 2004/0050341 A1 Mar. 18, 2004

Related U.S. Application Data

(63) Continuation-in-part of application No. 10/242,552, filed on Sep. 12, 2002, now Pat. No. 6,814,030, which is a continuation-in-part of application No. 10/242,551, filed on Sep. 12, 2002, which is a continuation-in-part of application No. 10/242,550, filed on Sep. 12, 2002, now Pat. No. 6,588,374.

(51) Int. Cl.$^7$ .............................................. A01N 25/00
(52) U.S. Cl. ..................................... 119/651; 424/405
(58) Field of Search ................................ 119/651, 656, 119/652, 660, 670, 673, 677; 514/471; 424/401, 402, 403, 404, 405–406

(56) References Cited

U.S. PATENT DOCUMENTS

| | | | |
|---|---|---|---|
| 5,434,181 A | * | 7/1995 | Kodaka et al. ............. 514/471 |
| 5,532,365 A | | 7/1996 | Kodaka et al. |
| 6,274,570 B1 | | 8/2001 | Vogt et al. |
| 6,479,542 B2 | | 11/2002 | Sembo et al. |
| 6,566,392 B1 | * | 5/2003 | Okada et al. ............... 514/461 |
| 6,588,374 B1 | | 7/2003 | Cottrell et al. |
| 2003/0013684 A1 | * | 1/2003 | Kawahara et al. ............ 514/75 |

FOREIGN PATENT DOCUMENTS

| | | |
|---|---|---|
| EP | 0 979 606 A1 | 2/2000 |
| JP | 3-220176 | 9/1991 |
| WO | WO 02/05639 A2 | 1/2002 |

OTHER PUBLICATIONS

U.S. Appl. No. 10/242,551, filed Sep. 2002, Cottrell, et al.
U.S. Appl. No. 10/242,552, filed Sep. 2002, Cottrell, et al.

* cited by examiner

Primary Examiner—Yvonne R. Abbott
(74) Attorney, Agent, or Firm—Stroock & Stroock & Lavan LLP

(57) ABSTRACT

A topical insecticide is provided which can be safe to use and avoids many common deleterious side effects of conventional topical insecticides. In one preferred embodiment of the invention, the active ingredient of the insecticide formulation is an amine derivative, having a nitro-methylene group, a nitroamino group or a cyanoamino group, which can be formulated to have low toxicity and excellent insecticidal activity. One particularly suitable insecticide is 1-{(tetrahydro-3-furanyl)methyl}-2-nitro-3-methylguanidine (dinotefuran), an aldulticide that will kill adult fleas combined with methoprene.

18 Claims, No Drawings

HIGH CONCENTRATION DINOTEFURAN FORMULATIONS CONTAINING METHOPRENE

CROSS REFERENCE TO RELATED APPLICATIONS

The present application is a continuation-in-part of U.S. Ser. No. 10/242,550, now U.S. Pat. No. 6,588,374, U.S. Ser. No. 10/242,551 and U.S. Ser. No. 10/242,552, now U.S. Pat. No. 6,814,030, all of which were filed Sep. 12, 2002. Priority is claimed to all of the applications listed above, which are incorporated herein by reference.

BACKGROUND OF INVENTION

The invention relates generally to insecticides and more particularly to a topical insecticide, such as one suitable to use on house pets such as cats and dogs.

The infestation of animals with fleas, ticks, flies and the like is highly undesirable. Accordingly, it has become common to administer both topical and internal insecticides to livestock and pets. Topical applications can be desirable, in that many insecticides are acceptably safe when used topically, but not when used internally.

Various topical insecticides have drawbacks. Some require a large volume to be applied to the animal. This can cause considerable mess and can lead to an unpleasant smell. Also, when the animal is a house pet, there is a further complication in that the insecticide should be safe for human contact. It should also not lead to staining of furniture, carpeting and the like. Finally, even if safe, topical insecticides for house pets should not be irritating or lead to rashes, hair loss or exhibit other unpleasant side effects.

Accordingly, it is desirable to provide an improved topical insecticide, which overcomes drawbacks of the prior art.

SUMMARY OF THE INVENTION

Generally speaking, in accordance with the invention, a topical insecticide is provided which can be safe to use and avoids many common deleterious side effects of conventional topical insecticides. In one preferred embodiment of the invention, the active ingredient of the insecticide formulation is an amine derivative, having a nitro-methylene group, a nitroamino group or a cyanoamino group, which can be formulated to have low toxicity and excellent insecticidal activity. Active ingredients of insecticides and their method of formation in accordance with the preferred embodiments of the invention are discussed in U.S. Pat. Nos. 5,532,365 and 5,434,181, and U.S. application Ser. Nos. 10/242,550, 10/242,551 and 10/242,552 filed on Sep. 12, 2002, the contents of which are incorporated herein by reference. One particularly suitable insecticide is 1-{(tetrahydro-3-furanyl)methyl}-2-nitro-3-methylguanidine (dinotefuran). Dinotefuran is an adulticide that will kill adult fleas.

In one preferred embodiment of the invention, the active portion of the insecticide formulation comprises (tetrahydro-3-furanyl)methylamine derivatives of following formula (1).

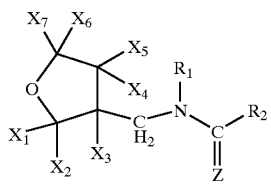

Active ingredients and insecticides in accordance with preferred embodiments of the invention are generally available as crystals and solids. Therefore, they need to be dissolved or otherwise put into a liquid form for use as topical spot products on animals. Topical spot products are more advantageous if the amount of liquid applied can be minimized. This must be balanced with the need for appropriate dosage to achieve the desired insecticidal effect. Therefore, it is desirable to use a solvent that will allow the solubilization of a high concentration of insecticide.

It is also desirable that the resulting formulation be stable (i.e., no crystallization) when stored at 0° F. and 40° F. for 1 month, which is important because these conditions can be met in commerce. The crystallization would reduce the amount of insecticide in solution and reduce the efficacy of the solution applied to the animal.

Phenyl methanol, is an alcohol, also known as benzyl alcohol, and is a liquid, somewhat soluble in water. It is routinely used in perfumes, flavors, photographic developers, dyes, films and inks and has other uses. It was surprisingly discovered that a relatively high concentration of the dinotefuran could be solubilized in phenyl methanol.

Methoprene is an insecticide that acts as an insect growth regulator that prevents flea eggs from hatching. It was unexpectedly determined that methoprene can act as a solubility enhancer for amine derivative insecticides such as dinotefuran, discussed above. For example, the addition of methoprene to the dinotefuran formulations with phenyl methanol allowed the preparation of more highly concentrated solutions of dinotefuran that do not crystallize at 0° F.

In one aspect of the current invention, the dinotefuran is dissolved in solvent containing methoprene to a concentration range of 5–25%, more preferably 9–20% and most preferably about 12.5 to 19.2%, with 17.5% as a preferred example. All percentages, unless otherwise evident, are on a weight basis.

The formulation can be applied as a topical drop about once per month, preferably in the area between the shoulder blades and the base of the skull to kill fleas and flea eggs for over a one month period.

Accordingly, it is an object of the invention to provide an improved topical insecticide, which overcomes drawbacks of the prior art.

DETAILED DESCRIPTION OF THE PREFERRED EMBODIMENTS

The novel (tetrahydro-3-furanyl)methylamine derivatives of the formula (1) have an excellent insecticidal activity even in the absence of a pyridylmethyl group or a thiazolylmethyl group in their molecular structure. According to the present invention, there are provided (tetrahydro-3-furanyl)methylamine derivatives represented by formula (1), where $X_1$, $X_2$, $X_3$, $X_4$, $X_5$, $X_6$ and $X_7$ represent each a hydrogen atom or an alkyl group having from 1 to 4 carbon atoms; $R_1$ represents a hydrogen atom, an alkyl group having from 1 to 5 carbon atoms, an alkenyl group having 3 carbon atoms, a benzyl group, an alkoxyalkyl group having from 2 to 4 carbon atoms (in its whole group), an alkyloxycarbonyl group having from 1 to 3 carbon atoms, a phenoxy carbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group or an N,N-dimethylcarbamoyl group; $R_2$ represents a hydrogen atom, an amino group, a methyl group, an alkylamino group having from 1 to 5 carbon atoms, a di-substituted alkylamino group having from 2 to 5 carbon atoms (in its whole group), a 1-pyrrolidinyl group, an alkenylamino group having 3 carbon atoms, an alkynylamino group having 3 carbon atoms, a methoxyamino group, an alkoxyalkylamino group having from 2 to 4 carbon atoms (in its whole group), a methylthio group or ——N($Y_1$)$Y_2$ (where $Y_1$ represents an alkyloxycarbonyl group having from 1 to 3 carbon atoms, a phenoxycarbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group, an N,N-dimethylcarbamoyl group, a (tetrahydro-3-furanyl)methyl group or a benzyl group, and $Y_2$ represents a hydrogen atom or an alkyl group having from 1 to 5 carbon atoms); and Z represents =N—$NO_2$, =CH—$NO_2$ or =N—CN; insecticides containing the derivatives as an effective ingredient; and intermediates for producing the compounds of the formula (1) represented by a formula (2):

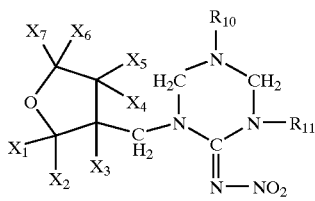

where $X_1$, $X_2$, $X_3$, $X_4$, $X_5$, $X_6$ and $X_7$ represent each a hydrogen atom or an alkyl group having from 1 to 4 carbon atoms; $R_{10}$ represents an alkyl group having from 1 to 5 carbon atoms or a benzyl group; and $R_{11}$ represents an alkyl group having from 1 to 5 carbon atoms or a benzyl group.

The novel (tetrahydro-3-furanyl)methylamine derivatives of the formula (1) and formula (2) according to the invention are excellent compounds having a high insecticidal power and broad insecticidal spectrum. Further, agricultural chemicals containing the novel (tetrahydro-3-furanyl) methylamine derivatives of the formula (1) and (2) according to the invention have outstanding characteristics as insecticides and hence are useful.

Specific examples of the alkyl group for $X_1$, $X_2$, $X_3$, $X_4$, $X_5$, $X_6$ and $X_7$ in the above formulae (1) and (2) include a methyl group, an ethyl group, an n-propyl group, an iso-propyl group, a tert-butyl group, and the like, preferably a methyl group.

Specific examples of the alkyl group for $R_1$ include a methyl group, an ethyl group, an n-propyl group, an iso-propyl group, an n-butyl group, an iso-butyl group, a sec-butyl group, a tert-butyl group, an n-pentyl group, and the like.

Specific examples of the alkenyl group for $R_1$ include a 1-propenyl group, a 2-propenyl group, and the like.

Specific examples of the alkoxyalkyl group for $R_1$ include a methoxymethyl group, an ethoxymethyl group, an n-propoxymethyl group, an iso-propoxymethyl group, a methoxyethyl group, an ethoxyethyl group, and the like.

Specific examples of the alkyloxycarbonyl group for $R_1$ include a methyloxycarbonyl group, an ethyloxycarbonyl group, an n-propyloxycarbonyl group, an iso-propyloxycarbonyl group, and the like.

Specific examples of the alkylcarbonyl group for $R_1$ include a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group, a tert-butylcarbonyl group, an n-pentylcarbonyl group, an n-hexylcarbonyl group, and the like.

Specific examples of the alkenylcarbonyl group for R1 include a vinylcarbonyl group, a 1-methylvinylcarbonyl group, and the like.

Specific examples of the cycloalkylcarbonyl group for $R_1$ include a cyclopropylcarbonyl group, a cyclobutylcarbonyl group, a cyclopentylcarbonyl group, a cyclohexylcarbonyl group, and the like.

Specific examples of the benzoyl group substituted by alkyl group(s) for $R_1$ include a 2-methylbenzoyl group, a 3-methylbenzoyl group, a 4-methylbenzoyl group, a 4-tertbutylbenzoyl group, and the like.

Specific examples of the benzoyl group substituted by halogen atom(s) for R1 include a 2-chlorobenzoyl group, a 3-chlorobenzoyl group, a 4-chlorobenzoyl group, a 3,4-dichloro-benzoyl group, a 4-fluorobenzoyl group, and the like.

Although $R_1$ can take various substituents as described above, it is preferably a hydrogen atom, an alkylcarbonyl group having from 1 to 4 carbon atoms or a cyclopropylcarbonyl group.

Specific examples of the alkylamino group for $R_2$ include a methylamino group, an ethylamino group, an n-propylamino group, an iso-propylamino group, an n-butylamino group, an iso-butylamino group, a sec-butylamino group, a tert-butylamino group, an n-pentylamino group, and the like, preferably a methylamino group.

Specific examples of the di-substituted alkylamino group for $R_2$ include a dimethylamino group, a diethylamino group, an N-methyl-N-ethylamino group, an N-methyl-N-n-propylamino group, an N-methyl-N-n-butylamino group, and the like, preferably a dimethylamino group.

Specific examples of the alkenylamino group for $R_2$ include a 1-propenylamino group, a 2-propenylamino group, and the like.

Specific examples of the alkynylamino group for $R_2$ include a propargylamino group, and the like.

Specific examples of the alkoxyalkylamino group for $R_2$ include a methoxymethylamino group, an ethoxymethylamino group, an n-propoxymethylamino group, an iso-propoxymethylamino group, a methoxyethylamino group, an ethoxyethylamino group, and the like.

Specific examples of the alkyloxycarbonyl group denoted by $Y_1$ for $R_2$ include a methyloxycarbonyl group, an ethyloxy-carbonyl group, an n-propyloxycarbonyl group, an iso-propyloxy-carbonyl group, and the like.

Specific examples of the alkylcarbonyl group denoted by $Y_1$ for $R_2$ include a methylcarbonyl group, an ethylcarbonyl group, an n-propylcarbonyl group, an iso-propylcarbonyl group, an n-butylcarbonyl group, an isobutylcarbonyl group, a sec-butylcarbonyl group, a tertbutylcarbonyl group, an n-pentylcarbonyl group, an n-hexylcarbonyl group, and the like, preferably a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group and a tert-butylcarbonyl group.

Specific examples of the alkenylcarbonyl group denoted by $Y_1$ for $R_2$ include a vinylcarbonyl group, a 1-methylvinylcarbonyl group, and the like.

Specific examples of the cycloalkylcarbonyl group denoted by $Y_1$ for $R_2$ include a cyclopropylcarbonyl group, a cyclobutylcarbonyl group, a cyclopentylcarbonyl group, a cyclohexylcarbonyl group, and the like, preferably a cyclopropyl-carbonyl group.

Specific examples of the benzoyl group substituted byalkyl group(s) denoted by $Y_1$ for $R_2$ include a 2-methylbenzoyl group, a 3-methylbenzoyl group, a 4-methylbenzoyl group, a 4-tert-butylbenzoyl group, and the like.

Specific examples of the benzoyl group substituted by halogen atom(s) denoted by $Y_1$ for $R_2$ include a 2-chlorobenzoyl group, a 3-chlorobenzoyl group, a 4-chlorobenzoyl group, a 3,4-dichlorobenzoyl group, a 4-fluoro benzoyl group, and the like.

Specific examples of the alkyl group denoted by $Y_2$ for $R_2$ include a methyl group, an ethyl group, an n-propyl group, an iso-propyl group, an n-butyl group, an iso-butyl group, a sec-butyl group, a tert-butyl group, an n-pentyl group, and the like, preferably a methyl group.

In the formula (1), compounds in which $R_1$ and $Y_1$ are concurrently an alkylcarbonyl group having from 1 to 4 carbon atoms or a cyclopropylcarbonyl group are preferred from the viewpoint of both insecticidal activity and production method.

In the development of a formulation for use on animals, there are several parameters that must be considered. These are:

(a) Concentration high enough to minimize the volume of the topical applied to the animal (one would not want to put 20 ml, e.g., onto a small cat).

(b) The formulation should be stable for one month at 130° F., 110° F., 40° F., room temperature and 0° F. This helps ensure that the formulation remains stable under the conditions that it could meet in commerce.

(c) Safe to use on the animal—particularly non-irritating since the product is applied to the skin. Also safe if ingested by the animal; ingestion can occur when cats groom themselves.

(d) Safe to use by the consumer.

(e) Efficacious in use—should kill greater than 90% of the fleas up to 28 days.

(f) Efficacy would be reduced if crystallization occurred in the package.

(g) Needs to be aesthetically pleasing—"no oily drop" on the animal when applied.

(h) Fast drying to reduce the chance of the animal shaking off the liquid thereby reducing efficacy.

(i) Microbiologically stable.

The above-referenced patents recognize different possible solvents, but do not provide information on how to formulate insecticide in a non-irritating manner. No examples were given in which the compounds were used on animals. Additionally, in all of the examples given the compounds were dissolved into solvents that are undesirable to use on animals. Specifically, acetone, used in all but one of the examples, is very irritating by both inhalation and skin contact, due to de-fatting action on skin and mucous membranes. It is also very irritating to the eyes. Accordingly, there is a need to develop a different solvent for these compounds that can be used on animals. The present formulation satisfies the parameters detailed above.

In one aspect of the current invention, the dinotefuran is dissolved in solvent containing methoprene to a concentration range of 5–25%, more preferably 9–20% and most preferably about 12.5 to 19.2%, with 17.5% as a preferred example. All percentages, unless otherwise evident, are on a weight basis. Methoprene is advantageously included as over 0.1%, advantageously about 0.1 to 3%. Advantageous weight ratios of dinotefuran:methoprene range from about 30:1 to 2.5:1, more preferably about 25:1 to 3:1.

The following examples are given for purposes of illustration only and are not intended to be construed in a limiting manner.

EXAMPLE 1

Preparation of 1-{(tetrahydro-3-furanyl)methyl}-2-nitro-3-methylguanidine(dinotefuran)

A mixture comprising 10.0 g of (tetrahydro-3-furanyl) methanol, 29.5 g of trifluoromethanesulfonic anhydride, 10.0 g of pyridine and 200 ml of dichloromethane was stirred for an hour at room temperature. Water was poured into the reaction solution to separate the organic layer, which was washed with 1 N hydrochloric acid, water and a saturated saline solution, dried, and concentrated to obtain 20 g of 3-tetrahydro-furanylmethyl triflate. 3.25 g of 60% sodium hydride were added to 12.5 g of 1,5-dimethyl-2-nitroiminohexahydro-1,3,5-triazine and 60 ml of DMF at room temperature, followed by stirring for an hour. 20.0 g of the 3-tetrahydrofuranylmethyl triflate were added thereto, and the mixture was stirred at 50° C. for 2 hours. After cooling the mixture to room temperature, 50 ml of 2N hydrochloric acid were added thereto, followed by stirring at 50° C. for 2 hours. The resultant mixture was neutralized with sodium bicarbonate and extracted with dichloromethane, and the extract was dried and concentrated. The residue thus obtained was purified by silica gel column chromatography (eluent: ethyl acetate/hexane=1/1) to obtain 7.8 g of 1-{(tetrahydro-3-furanyl)methyl}-2-nitro-3-methylguanidine(dinotefuran).

EXAMPLE 2

Preparation of Insecticide Formulation Containing Dinotefuran, Ethanol and Water 5 g (i.e., 5.6% (weight/weight)) of dinotefuran was dissolved into 100 ml of a mixture comprising 70% ethanol and 30% water. The resulting mixture can be spot applied to companion animals, such as dogs and cats and will kill fleas, ticks and other insects.

EXAMPLE 3

Preparation of Insecticide Formulation Containing Dinotefuran and Phenyl Methanol 15 g (i.e., 12.5% (weight/weight)) of dinotefuran was dissolved into 100 ml of phenyl methanol. The resulting solution can be spot applied to companion animals, such as dogs and cats and will kill fleas, ticks and other insects.

EXAMPLE 4

Preparation of Insecticide Formulation Containing Dinotefuran, Pyriproxyfen and Phenyl Methanol 20 g of dinotefuran was added to 100 ml phenyl methanol with stirring until it dissolves. 3 g of pyriproxyfen was added to the solution with stirring to produce a clear, homogeneous solution.

EXAMPLE 5

Preparation of Insecticide Formulation Containing Dinotefuran, Pyriproxyfen and Phenyl Methanol 25 g of dinotefuran was added to 100 ml phenyl methanol with stirring until it dissolved. 1 g of pyriproxyfen was added to the solution with stirring to produce a clear, homogeneous solution of high insecticide concentration.

The resulting solution can be spot applied to companion animals, such as dogs and cats and will kill fleas, ticks and other insects.

EXAMPLE 6

Stability of Dinotefuran/Pyriproxyfen Formulations

Table 1 demonstrates that an approximate 50% increase in concentration can be achieved for dinotefuran by including pyriproxyfen at low levels in the formulation based on the criterion of no crystal formation at 0° F. during a 1 month period.

TABLE 1

| Formulation Stability Studies (% are w/w) | | | |
|---|---|---|---|
| Dinotefuran | Pyriproxyfen | Phenyl Methanol | Stable |
| 12.5 | 0 | 87.5 | Yes |
| 14.7 | 0 | 85.3 | No* |
| 15.7 | 2.4 | 81.9 | Yes |
| 15.9 | 0.8 | 83.3 | Yes |
| 19.2 | 0.8 | 80.0 | Yes |

*Crystallizes at 0° F.

EXAMPLE 7

Preparation of Insecticide Formulation Containing Dinotefuran, Methoprene and Phenyl Methanol 20 g of dinotefuran was added to 100 ml phenyl methanol with stirring until it dissolved. 1 g of methoprene was added to the solution with stirring to produce a clear, homogeneous solution of high insecticide concentration.

EXAMPLE 8

Preparation of Insecticide Formulation Containing Dinotefuran, Methoprene and Phenyl Methanol 18 g of dinotefuran was added to 100 ml phenyl methanol with stirring until it dissolved. 1 g of methoprene was added to the solution with stirring to produce a clear, homogeneous solution of high insecticide concentration.

EXAMPLE 9

Preparation of Insecticide Formulation Containing Dinotefuran, Methoprene and Phenyl Methanol 16 g of dinotefuran was added to 100 ml phenyl methanol with stirring until it dissolved. 1 g of methoprene was added to the solution with stirring to produce a clear, homogeneous solution of high insecticide concentration.

EXAMPLE 10

Stability of Dinotefuran/Methoprene Formulations

TABLE 2

| Formulation Stability Studies (% are w/w) | | | |
|---|---|---|---|
| Dinotefuran | Methoprene | Phenyl Methanol | Stable |
| 12.5 | 0 | 87.5 | Yes |
| 14.7 | 0 | 85.3 | No* |
| 19.2 | 0.8 | 80.0 | No* |
| 18.5 | 0.8 | 80.7 | Yes |
| 17.5 | 0.8 | 81.7 | Yes |
| 16.0 | 0.8 | 83.2 | Yes |
| 14.6 | 0.8 | 84.6 | Yes |
| 12.9 | 3.2 | 83.9 | Yes |
| 12.1 | 4.0 | 83.9 | Yes |

*Crystallizes at 0° F.

It has been determined that the concentration of dinotefuran can be increased up to 50% and more by including methoprene, even at low levels of about 0.8% and below, compared to a similar formulation without methoprene. Also, inclusion of methoprene up to and over 4% are stable. Typically, dinotefuran concentration of over about 8% will crystallize at 0° F. within a few days.

EXAMPLE 11

In Vivo Activity of a Flea Dermal Treatment Against the Cat Flea (*Ctenocephalides felis*) on Cats Eighteen cats were separated into three groups each containing 6 cats. Group 1 (6 cats each weighing 9 lbs. or less) remained untreated as Non-Treated Controls. Group 2 (6 cats each over 9 lbs.) were treated with 3.4 ml of the dinotefuran insecticide formulation (5.71% w/w). Group 3 (6 cats each weighing 9 lbs. or less) were treated with 1.5 ml of the dinotefuran insecticide formulation (5.71% w/w).

Approximately 18 hours prior to treatment the cats were infested with 100 cat fleas (*Ctenocephalides felis*) which were applied to the animal's back. Cats in Groups 2 and 3 were then treated with the indicated volume of insecticide by dispensing the liquid at skin level between the shoulder blades. Flea counts were taken at day 1 (i.e., 24 hours post-treatment), day 8, day 15, day 22 and day 29. Cats were re-infested with 100 fleas on days 7, 14, 21, and 28. To determine the efficacy of the dermal treatment, the number of fleas found on treated cats was compared to the number of fleas found on untreated cats. Percent reduction was determined as follows and the results are summarized in Table 2:

$$\frac{\text{Mean Number of fleas on Untreated Cats} - \text{Mean Number of fleas on Treated Cats}}{\text{Mean Number of fleas on Untreated Cats}} \times 100\%$$

As shown in Table 2 the results demonstrate that the dosages used on Groups 2 and 3 are both effective at reducing the number of adult fleas on cats through at least 29 days and thus are effective as a one month dermal treatment.

TABLE 3

Controlled Percent Reduction in Flea Population

|  | Day 1 | Day 8 | Day 15 | Day 22 | Day 29 |
|---|---|---|---|---|---|
| Control Group 1 | 0 | 0 | 0 | 0 | 0 |
| Group 2 | 100 | 100 | 99 | 99 | 96 |
| Group 3 | 100 | 98 | 95 | 95 | 91 |

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. An insecticide formulated by dissolving an insecticidably effective amount of dinotefuran in an effective amount of an alcohol-based solvent component, said solvent component comprising sufficient methoprene to increase the solvency of the dinotefuran in the solvent component compared to the solvency of the dinotefuran in the solvent component without the methoprene and to increase the effectiveness of the insecticide compared to its effectiveness without the methoprene, wherein there is sufficient dinotefuran that it would crystallize and precipitate out of solution, within one month at 0° F., if the methoprene were removed from the formulation.

2. The insecticide of claim 1, wherein said solvent component comprises phenyl methanol.

3. The insecticide of claim 2, wherein said dinotefuran is dissolved in the formulation to a concentration of about 9 to 20%.

4. The insecticide of claim 3, comprising over 0.1% methoprene.

5. The insecticide of claim 3, comprising about 0.1 to 3% methoprene.

6. The insecticide of claim 3, wherein the formulation is not irritating to dogs or cats and is effective to kill fleas with applications of less than 20 ml to a cat.

7. The insecticide of claim 3, wherein one drop of the formulation is effective to kill fleas on a cat for at least one month.

8. The insecticide of claim 2, wherein the formulation is not irritating to dogs or cats and is effective to kill fleas with applications of less than 20 ml to a cat.

9. The insecticide of claim 2, wherein one drop of the formulation is effective to kill fleas on a cat for at least one month.

10. The insecticide of claim 1, wherein said dinotefuran is dissolved in the formulation to a concentration of about 5 to 25%.

11. The insecticide of claim 1, wherein the formulation is not irritating to dogs or cats and is effective to kill fleas with applications of less than 20 ml to a cat.

12. The insecticide of claim 1, wherein one drop of the formulation is effective to kill fleas on a cat for at least one month.

13. A method of controlling insect infestation in animals, comprising dissolving dinotefuran in a solvent component comprising methoprene and applying an insecticidably effective amount of the solution to an animal, wherein the solvent component contains sufficient dinotefuran to crystallize and precipitate after one month at 0° F. if the methoprene were removed from the solvent component in the formulation.

14. The method of claim 13, wherein the animal is a cat or a dog.

15. The method of claim 14, wherein the insect is a flea.

16. The method of claim 13, wherein the solvent component comprises phenyl methanol.

17. A method of preparing an insecticide formulation, comprising dissolving an insecticide in a composition comprising methoprene, wherein at least a portion of the insecticide is dissolved by the methoprene, wherein there is sufficient insecticide to crystallize and precipitate after one month at 0° F. if the methoprene were removed from the formulation.

18. The method of claim 17, wherein the solvent component comprises phenyl methanol.

* * * * *